United States Patent [19]

Gronowitz et al.

[11] Patent Number: 4,637,977
[45] Date of Patent: Jan. 20, 1987

[54] METHOD OF DETERMINING DTK ISOENZYME ACTIVITY AND THE USE THEREOF

[76] Inventors: Jan S. Gronowitz, Pettbols skola, Pl 2670, S-740 73 Hargshamn; Clas F. R. Källander, Vallby Husbyborg, S-755 90 Uppsala, both of Sweden

[21] Appl. No.: 576,375
[22] PCT Filed: May 10, 1983
[86] PCT No.: PCT/SE83/00190
§ 371 Date: Jan. 5, 1984
§ 102(e) Date: Jan. 5, 1984
[87] PCT Pub. No.: WO83/04054
PCT Pub. Date: Nov. 24, 1983

[30] Foreign Application Priority Data

May 14, 1982 [SE] Sweden ............................. 8203041

[51] Int. Cl.$^4$ ............................................. C12Q 1/48
[52] U.S. Cl. ............................................. 435/15; 435/5; 435/29; 435/34
[58] Field of Search .................... 435/5, 15, 29, 34, 35

[56] References Cited

U.S. PATENT DOCUMENTS

4,302,535 11/1981 Skopek et al.

FOREIGN PATENT DOCUMENTS

0042482A1 12/1981 European Pat. Off.

OTHER PUBLICATIONS

Infection and Immunity, vol. 36, pp. 30–37, published Apr. 1982 (Kallander, C. F. R. et al.) "Human Serum Antibodies to Carcella–Zoster Virus Thymidine Kinase).
Infection and Immunity, vol. 29, pp. 425–434, published Aug. 1980, (Gronowitz, J. S., Kallander C. F. R.) "Optimized Assay for Thymidine Kinase and its Application to the Detection of Antibodies Against Herpes Simplex Virus Type 1- and 2-Induced Thymidine Kinase).
Journal of Biological Chemistry, vol. 254, pp. 10747–10753, published Nov. 10, 1979 (Chen, M. S. et al.) "Kinetic Studies of Herpes Simplex Virus Type 1-Encoded Thymidine and Thymidylate Kinase, a Multifunctional Enzyme".
Biochimica et Biophysica Acta, vol. 452, pp. 370–381, published 1976 (Cheng Y–C) "Deoxythymidine Kinase Induced in HeLa TK–Cells by Herpes Simplex Virus Type 1 and Type 2".
J. Med. Chem., vol. 23, pp. 962–964 published 1980 (Nakayama, C. et al.) "Thymidine Phosphorylase, Substrate Specificity for 5–Substituted 2–Deozyuridines".
Chemical Abstracts, vol. 96 (1982), Abstract No. 138542s, Izotoptechnike 1981, 24 (3), 109–118.

Primary Examiner—Christine M. Nucker
Assistant Examiner—Stephen C. Wieder
Attorney, Agent, or Firm—Bacon & Thomas

[57] ABSTRACT

A method of determining dTk isoenzyme levels of a human or animal body fluid or cell sample is disclosed, which comprises the steps of reacting said sample with a substrate for said isoenzyme in the presence of a phosphate donor and a buffer system, and measuring the amount of phosphorylated product formed, said amount being proportional to said isoenzyme level. The method is characterized by using in combination (a) a buffer system at pH ranging from 5 to 9 and being present in a concentration of no more than 250 mM,
(b) a substrate consisting of 2'-deoxy-5-halouridin, part of which has a radio-labelled 5-halogen, and being present in a concentration ranging from $2 \times 10^{-9}$–$5 \times 10^{-6}$M, and
(c) the phosphate donor being present in a concentration not exceeding 20 mM.

The sensitivity of the method permits measurement of minute amounts of dTk, and the method can be used for e.g. diagnosis, prognostics and monitoring of diseases involving altered ATP mediated dTk activity, such as cancers, tumors, and certain virus infections, or alterated CTP mediated dTk activity, such as HSV type 1, type 2, and VZV infections.

8 Claims, 16 Drawing Figures

METHOD OF DETERMINING DTK ISOENZYME ACTIVITY AND THE USE THEREOF

The present invention relates to a method of determining the levels of the isoenzyme dTk (deoxythymidine kinase) in human or animal body fluids or cell samples. The invention further relates to the use of said method for the diagnosis and prognostics of diseases dominated by ATP (adenosinetriphosphate) mediated dTk activity, such as cancers, tumours and certain viral infections as well as of diseases characterized by CTP (cytidinetriphosphate) mediated dTk activity, such as HSV (Herpes Simplex Virus) type 1 and type 2 and VZV (Varicells Zoster Virus) infections. The invention also relates to the use of said method for dTk isoenzyme typing.

BACKGROUND OF THE INVENTION

The enzyme deoxythymidine kinase (dTk) provides the eucaryotic cell with a means for utilizing deoxythymidine (dT), which is not an intermediate in the thymidylate synthesis de novo. For this reason dTk is considered a salvage enzyme, introducing dT into the DNA metabolism. As the major dTk form of mammalian cell is only present during cell division, the dTk has been denominated scavenger enzyme.

Three different cellular isoenzymes in human cells have been described. The cytosolar dTk, called dTk-F, which occurs in optimal amounts in dividing cells (stages G1 to S) (Bello, *Exptl. Cell Res.* 89: 263, 1974; Littlefield, *Biochim. Biophys. Acta.* 115: 398, 1966) and is more or less absent in resting cells. In humans this enzyme is coded for in chromosome 17 near the galactokinase locus. The second cellular isoenzyme is the mitochondrial, denominated dTk-A, which is present in the mitochondrial matrix. The activity of this dTk remains relatively constant during the different cell stages (Adelstein et al; *Develop. Biol.* 216: 537, 1971), and dTk-A is coded for by chromosome 16. The third dTk, a minor activity called dTk-B, has only been reported in continuous cell lines HeLa and KB and is said to be confined to the inside of the mitochondrial membrane (reviewed by Kit, *Pharmacol. Ther.* 4: 501, 1979).

The three cellular dTks differ in biochemical properties. The dTk-F and dTk-B, which are quite similar, are distinguished, besides as to localization, by isoelectric focusing, having different pI, and by electrophoretic mobility. In contrast to dTk-F and dTk-B, the dTk-A accepts cytidinetriphosphate (CTP) as a phosphate donor and is not as sensitive as the others to dTTP (deoxythymidinetriphosphate) feedback inhibition. The dTk-A also phosphorylates deoxycytidine (dC) and is inhibited by dCTP (reviewed by Kit, *Pharmacol. Ther.* (4: 501, 1979).

With regard to viruses, specific isoenzymes, coded by the viral genome, have been shown in the cell after infection with viruses from the Herpes group and the Pox group. Enzymatically the human virus specific dTks resemble dTk-A, except for the vaccinia dTk which cannot utilize CTP as phosphate donor and not either can phosphorylate deoxycytidine. This dTk is easily distinguished from the human cellular dTks by electrophoresis (Kit et al., *Progr. Med. Virol.* 21: 13, Karger Basel 1975). Both the HSV dTks and the VZV dTk have a broader spectrum of possible phosphate donors and accept different pyrimidines and pyrimidine analogues as substrates (Cheng et al, *Biochim. Biophys. Acta.* 452: 370, 1976, and *J. Virol.* 31: 172, 1979). The competitive blocking of dTk isoenzyme mediated dT conversion to dTmp (deoxythymidinemonophosphate) exerted by the dT-analogue 2'-deoxy-5-iodourine (IUdR), has been known for a long time. The use of radio-labeled IUdR directly as a substrate to gain high sensitivity in assays of viral dTks was shown by us (Gronowitz & Källander, *Infec. Immun.* 29: 425, 1980).

As mentioned dTk-F occurrence in cells is coupled to cell proliferation, and it is more or less absent in the differentiated cell (Munch-Petersen & Tyrsted, *Biochim. Biophys.* 478: 364, 1977). Studies of dTk activity in transplantable mouse tumours have revealed high dTk activities with correlation to growth rate (Bresnick et al, *Cancer Res.* 29: 1969, and *Cancer Res.* 31: 743, 1971). Recent reports have demonstrated enhanced dTk-F in peripheral blood lymphocytes of some patients suffering from malignant non-Hodkin's lymphoma and lymphatic leukemia (Ellims et al, *Cancer Res.* 41: 691 and *Brit. J. Haematol.* 49: 479, 1981). These researchers have also shown enhanced serum dTk levels in some patients from the non-Hodkin's group (Ellims et al, *Blood* 58: 926, 1981). Due to the conventional dTk assay used, employing $^3$H-dT in high concentration ($5 \times 10^{-6}$M), dTk activity could only be found in a few patients with advanced disease. Further the dTk activity could be evaluated as a prognostic marker only if differential analysis regarding dTk-F and dTk-A was performed.

Conventionally dTk activity has thus been measured by following the conversion of either $^3$H- or $^{14}$C-labeled dT to dTmp with ATP as the phosphate donor. We have recently designed an improved dTk assay system for viral dTk isoenzymes, which uses $^{125}$I-Iododeoxyuridine (IUdR) as the substrate. The improved sensitivity obtained allowed the detection of dTk from as little as 25 HSV-infected cells. In contrast the conventional assay based on the use of $^3$H-dT, at a normally used concentration of $10^{-5}$M, would require at least 450 times more enzyme. However, even though being useful in studies of viral dTks this improved assay system was not appropriate for long time assays of cellular dTk-F, partly due to the instability of this enzyme. The inability of this method of detecting the presence of minute dTk amounts in serum is easily extracted from the studies over occurrence of virus dTk blocking antibodies (dTk-ab). In these studies more than 275 human sera were assayed for dTk-ab but disturbing serum dTk activities were found in only two cases (Gronowitz & Källander, *Infec. Immun.* 29: 425, 1980; Gronowitz & Källander, *J. Med. Virol.* 8: 177, 1981; Källander et al, *Infec. Immun.* 36: 30, 1982).

SUMMARY OF THE INVENTION

It is an object of the present invention to provide a means for the diagnosis of certain virus infections and malignant tumours, including the monitoring of the malignancies for different purposes.

A further object of the invention is to provide a sensitive assay system capable of detecting minute amounts of dTk present in human and animal body fluids and cell samples, e.g. in serum, blister secretes, spinal fluid, vesicle fluid, and similar clinical specimens, which system is also designed to minimize the contribution of cellular dTk-A.

A further object of the invention is to provide a method of assaying for dTk-F for use in the detection and prognostics of tumour diseases, and for the monitoring of alterations in the disease, and detection of relapses.

A still further object of the invention is the use of said assay method in the evaluation of metastases in connection with lung cancer of the oat cell type.

Still another object of the invention is the use of said assay method in connection with leukemia for determining, by measurement of dTk present in spinal fluid, if metastases are present in the cerebro-spinal system.

Another object of the invention is the use of said assay method as a group specific marker for certain infections in connection with viral diseases.

A further object of the invention is the use of a modification of said assay method for achieving specific detection of herpes virus specific dTks present in e.g. serum or vesicle fluid.

The above and other objects of the invention will be explained in detail in the following description of the assay method and its applications according to the invention.

The invention thus provides an improved assay system for the measurement of dTk levels, especially dTk-F levels in e.g. serum. This assay system is considerably more sensitive than prior art systems, and it has been found that the sensitivity is so high, that it is possible to use the assay system, which is very simple to practice, not only for determining pathological dTk levels, but even normal levels in healthy individuals (compare FIGS. 1 and 6). This assay system was not only found to be very sensive and reproducible for dTk-F determinations, giving linear turnovers for more than two hours, but was also found to give 2-6 times higher turnovers than prior art systems with the viral dTks. Another important advantage, compared to the conventional assay system, is the comparatively low turnover of dTk-A, this isoenzyme giving minimal contribution when measuring dTk-F or viral dTk in non-purified samples.

A variant of this assay system, using CTP instead of ATP as the phosphate donor, was found to be useful for specific detection of herpes virus induced dTk when samples to be analysed were preincubated with anit-herpes viruses dTk blocking sera.

The advantageous and unexpected technical effects described herein are according to the invention obtained by the use of a combination of a buffer system of low concentration and ionic strength, a specific type of radio-labelled substrate, which is present in low concentration, and a low concentration of a phosphate donor.

In its broadest aspect the invention relates to a method of determining dTk isoenzyme levels in a human or animal body fluid or cell sample wherein said sample is reacted with a substrate for said isoenzyme in the presence of a phosphate donor and a buffer system, and wherein the amount of phosporylated product formed is measured, said amount being proportional to said isoenzyme level. According to the invention said method is characterized by using, in combination.
  (a) a buffer system at pH ranging from 5 to 9 and being present in a concentration of no more than 250 mM,
  (b) a substrate consisting of 2'-deoxy-5-halouridin, part of which has a radiolabelled 5-halogen, and being present in a concentration ranging from $2\times10^{-9}$–$5\times10^{-6}$M, and
  (c) the phosphate donor being present in a concentration not exceeding 20 mM.

Figure 1A:
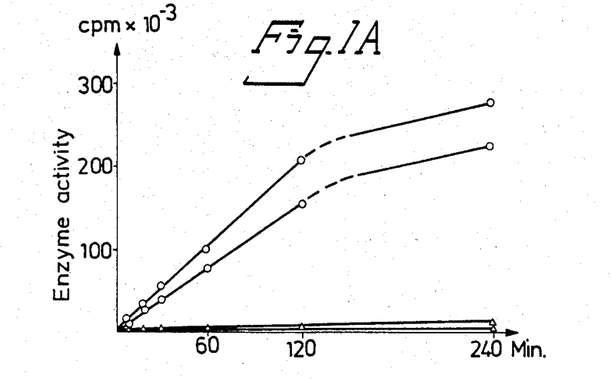
FIGS. 1A and B are diagrams showing enzyme activity plotted against time and illustrating the drastically improved sensitivity of the claimed method compared to the closest prior art.
Figure 1B:
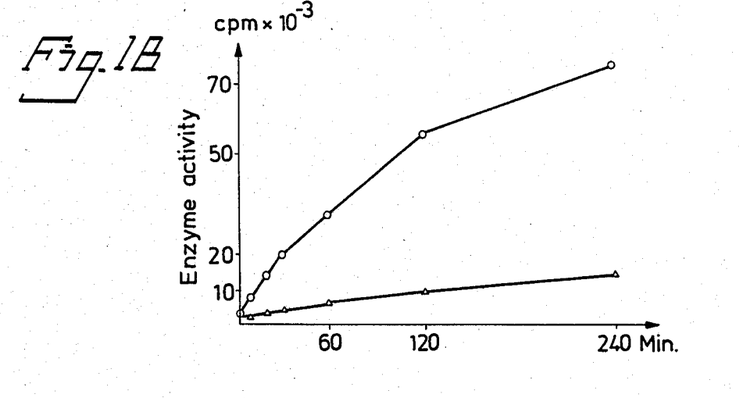

In contrast to the earlier described assay system using $^{125}$I-IUdR as substrate, the assay system according to the invention gives a linear turnover of substrate for the cellular dTk-F for more than two hours, and the detection sensitivity was drastically increased, as can be seen in FIG. 1. This Figure is a comparison between the assay system according to the invention (—o—o—o) and said prior art assay system (—Δ—Δ—Δ—) (Gronowitz and Källander, Infec. Immun. 29: 425, 1980). A=two sera containing human dTk-F originating from patients with leukemia. B=HSV type 2 dTk of cell culture origin. Total available $^{125}$I-IUdR was $550\times10^3$ cpm.

DESCRIPTION OF PREFERRED EMBODIMENTS

In a preferred embodiment of the invention said buffer system is present in a concentration of less than about 150 mM, especially being about 100 mM. The pH of the buffer is preferably in the range 6.5-8, especially about 7.4. The best results have been·obtained with buffers devoid of maleate, and lacking reactive or primary amino groups, in particular buffers substantially devoid of TRIS-maleate, HEPES buffer being the especially preferred buffer.

The substrate should be a radio-labelled thymidine analogue, especially a 2'-deoxy-5-halogen-uridine, wherein the label preferably is a reactive halogen isotop. The preferred substrate is $^{125}$I-2'-deoxy-5-iodouridine. The preferred substrate concentration is in the range of $1 \times 10^{-8}$–$5 \times 10^{-7}$M, especially about $10^{-7}$M.

The preferred phosphate donor for dTk-F determination is ATP, and the preferred phosphate donor for viral dTk determination is CTP. The preferred concentration of the phosphate donor is less than about 10 mM, especially about 0.5–5 mM. Phosphate donors known per se to have the same isoenzyme specificity as ATP and CTP may also be used.

$Mg^{2+}$ should preferably be present in at least equimolar concentration relative to the phosphate donor. A reducing agent, such as dithiothreitol, is preferably also present.

The measurement of the phosphorylated product can be made by procedures known per se (see e.g. Gronowitz et källander, *Infec. Immun.* 29: 425, 1980).

The application of the assay system according to the invention for detection of dTk activities in clinical specimens, e.g. serum or blister secrete, provided a new tool for diagnosis of certain virus infections, and malignancies. Also, normal serum dTk levels (e.g. >10 units), obtained with a single dTk assay with the procedure described, were found to be an excellent marker for prognostic use and so also sequential dTk values in monotoring the progression or regression of malignant disease. Furthermore in these patients serum dTk levels were useful as a marker of relapses and in evaluation of therapy effects. All, as exemplified below.

In the preferred embodiment, which has been practiced when performing the tests reported below, $^{125}$I-IUdR is used as the substrate. The composition and proportions, including final concentrations, of the preferred assay system are shown in Table 1 below.

TABLE 1

| Composition of buffer used in dTk assay | | |
|---|---|---|
| Component | Assay mixture | Final concentration[a] |
| [b]HEPES | 0.1 M | 86 mM |
| MgCl$_2$ | 17 mM | 15 mM |
| KCl | 20 mM | 17 mM |
| NaF | 1,2 mM | 1,0 mM |
| ATP | 4.6 mM | 3.9 mM |
| Dithiothreitol | 2.7 mM | 2.3 mM |
| Bovine Albumine | 0.33 mg/ml | 0.28 mg/ml |
| Glycerol | 6.6% | 5.7% |
| JUdR | — | $1.1 \times 10^{-7}$ M |
| pH | 7.4 | 7.4 |

[a]Proportions of one double sample is: 51.5 μl assay mixture, 6 μl of substrate solution (final concentration of $^{125}$I-JUdR $1 \times 10^{-7}$ M, 130–160 Ci/mM), and 2.5 μl of enzyme solution e.g. serum (added when starting the reaction), giving a final volume of 60 μl.
[b]N—2-hydroxyethylpiperazine N—2-ethanesulfonic acid.

In general, one double sample is prepared, consisting of 51.5 μl reaction solution, which is mixed with 6 μl substrate solution immediately before use. The reaction is then started by addition of 2.5 μl enzyme solution (e.g. serum sample). From this standard volume of a total of 60 μl, two samples of each 25 μl are taken. The composition of assay mixtures for experiments consisting of several double samples, taken after different incubation times, are calculated by multiplying the volumes of the components in the standard solution with the desired number of double samples. The assay is performed at 37° C. and all components are prewarmed 2 minutes before starting the reaction. The enzyme reaction is terminated by pipetting the sample onto a 1 cm² piece of Whatman DEAE-81 paper kept at 90°–100° C. To separate the product from the substrate, the paper is washed four times in 6 mM ammoniumformate solution, once in distilled water and finally in methanol. The washings are performed in 1 liter glass vessels kept on magnetic stirring. 10–15 paper discs, kept in a colander, are processed simultaneously. The colander is moved to a new washing bath every five minutes. Finally the paper discs are counted in an automatized gamma counter.

Figure 2A:
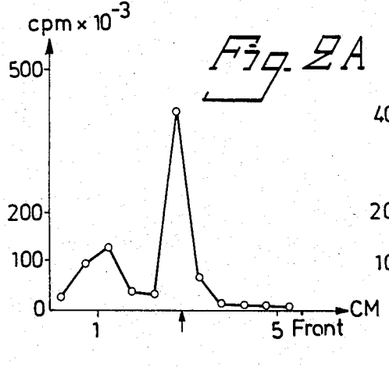
FIGS. 2A and B illustrate—by way of tlc graphs—the reduction in radiochemical purity of the preferred substrate according to the invention, $^{125}$I-IUdR, on storage.
Figure 2B:
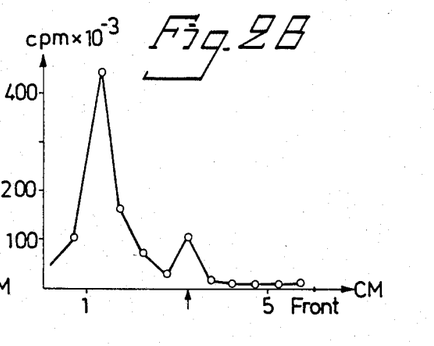
Figures 3, 4:
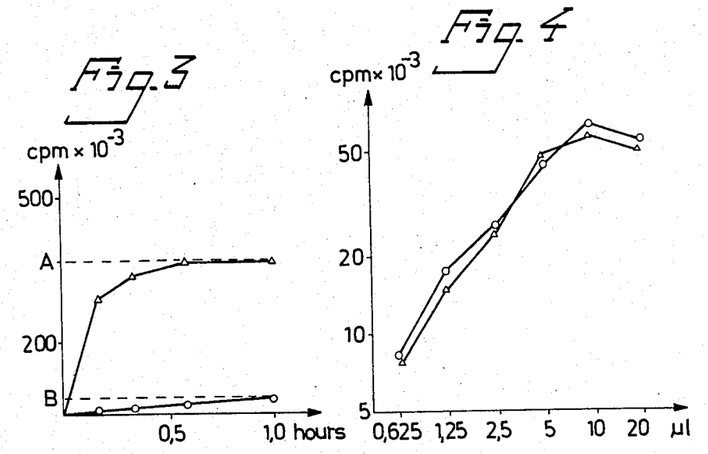
FIG. 3 is a diagram illustrating the calculation of enzyme activity in units when using an internal substrate control.
FIG. 4 is a diagram illustrating the inhibitory effeft of high serum concentrations in dTk measurements.

In order to eliminate day-to-day variation in the dTk assay, the reaction velocities obtained were recalculated to units. The reason for utilizing units in defining enzyme quantities is the variation in initial radiochemical purity, combined with the found biological decay of commercially available $^{125}$I-IUdR, which makes total radioactivity added per samle non-relevant for enzyme activity calculations. See FIG. 2, which shows separation of batches of commercially obtained $^{125}$I-IUdR on thin layer chromatography using precoated silica gel plates (Merck 60 F$_{254}$). 15% methanol, 85% chloroform was used as eluent. A=profiles at day of delivery, indicating 62% radiochemical purity. B=the same batch after 150 days in refrigerator. Initially >90% radiochemical purity was claimed by the manufacturers. Instead, an internal biologic control, measuring accessible radioactivity, was included in each assay. This control was a 100-fold excess of an HSV type 2 dtK preparation, giving extensive substate exhaustion. The amount of radioactivity incorporated in a 1 hour assay by this control was found to be about 85% of the values of intact $^{125}$I-IUdR, as calculated from thin layer chromatography. Considering the level (85%) found for the boilogical control, 1 unit of enzyme will be the enzyme amount converting $4.3 \times 10^{-15}$ moles of substrate per hour (under the conditions described). This relationship between unit and approximative molar turnover was chosen, as 1 unit will practically be expressed as about 1000 cpm, with the amount of isotope normally used (cf. Table 1). Another advantage with this biological isotope control, as it is processed in the same manner as the test samples, is that possible variations in units due to variations in product recovery are eliminated. The procedure for the calculation of units is exemplified in FIG. 3. Values for both the sample (—o—o—) and the control (—Δ—Δ—) are shown. A is the value of the internal control in cpm, which is proportional to the total available radiolabeled substrate. B is the value of product formed by the investigated sample expressed as cpm per hour.

$$\text{Units}(U) = \frac{B \times (S) \times v}{A \times 5.3 \times 10^{-15}},$$

where (S) is the substrate concentration (M), and v is the sample volume (liters).

Determination of serum dTk activities

Quantification of serum dTk was done in microtiter plates. For every 20 serum samples, background controls and an internal substrate control (see above) were included, and the set was subsequently processed as a unit. The amounts of serum sample used were 5 μl (or less per 120 μl final volume, as more serum might be inhibitory See FIG. 4. dTk activities were determined by sampling at 120 minutes. Enzyme activity as plotted against serum concentration per 60 μl sample. (o—o) serum from an individual suffering from NHL, (Δ—Δ) serum from an individual suffering from active CLL. This inhibitory effect is probably due to the presence of nucleotides or nucleosides, such as e.g. thymidine, thymidinetriphosphate, or catabolic enzymes present in some sera. Double samples were taken after 60 and 120 minutes. Medium turn-over, per hour and 25 μl sample, after correction for background, was calculated from each double sample separately. The average velocity value of the 60 and 120 minutes sampling was then determined, and used in further calculations (see above), if <20% variation was found.

Determination of dTk activities present in spinal fluid

Essentially the same procedure as for serum was used. The specific activity of $^{125}$I-IUdR was increased to around 320 Ci/mM. Spinal fluids may be concentrated before the enzyme determinations.

Qualitative determination of dTk isoenzymes

Figure 5:
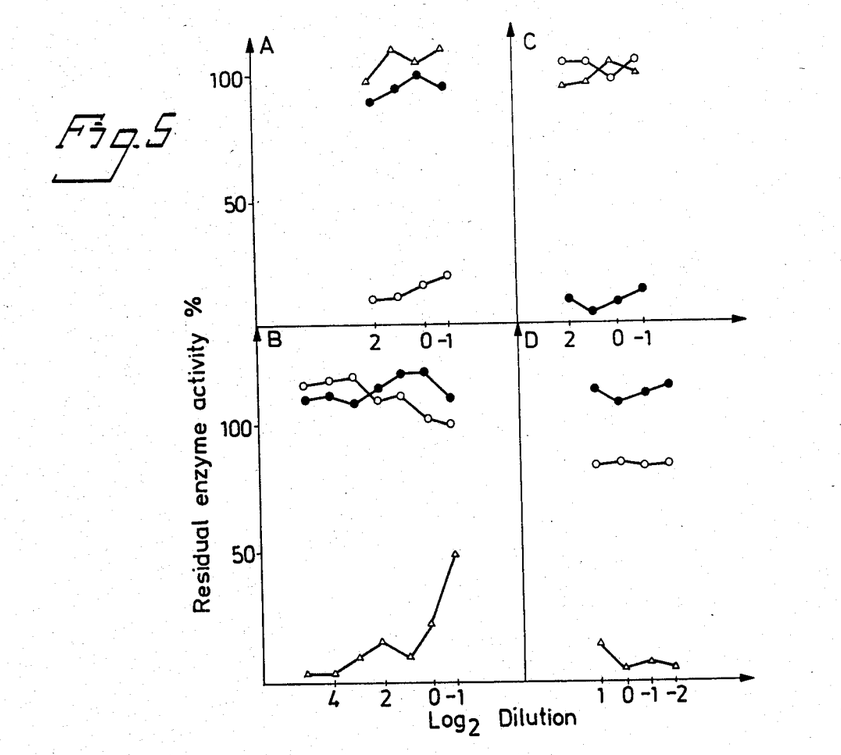
FIG. 5 illustrates—by way of diagrams—the typing of viral dTk in different clinical specimens.

Clincal specimens, e.g. vesicle fluids or serum, containing dTk activity were preincubated with isoenzyme specific dTk blocking antibody and residual enzyme activity was determined according to the procedure described above. ATP in the assay mixture was replaced by CTP, resulting in exclusion of dTk-F activity. The specimens to be investigated were serially twofold diluted (usually starting at 1:6) in reaction solution, and 15 μl was transferred from each dilution to four wells in a micro titer plate, in order to achieve four identical dilution sets. Prediluted VZV dTk-blocking serum (25 ml) was added to one well, a HSV type 1 dTk-blocking serum to a second well, a HSV type 2 dTk-blocking serum to a third well and to the last well a negative serum. The mixtures were incubated at 37° C. for 90 min., allowing the enzyme-antibody reaction to occur. Then the residual enzyme activities were determined. The reaction was started by the addition of 20 μl of a solution composed of 6 μl substrate solution mixed with 14 μl reaction solution. For each dilution the values obtained in the presence of the different antisera were recalculated as the percentage of the values obtained with the negative serum. Examples of such residual enzyme activities plotted against the log$_2$ dilution of specimens are shown in FIG. 5, wherein the residual activity after incubation with anti-VZV dTk serum (Δ—Δ), anti-HSV type 1 dTk (serum ●—●), and anti-HSV type 2 serum (o—o) in relation to control incubation with negative serum is plotted against different dilutions of the following samples: A=vesicle fluid from an individual suffering from an HSV type 2 infection; B=vesicle fluid from an individual suffering from an VZV infection; C=vesicle fluid from an individual suffering from HSV type 1 infection; D=serum from an individual suffering from VZV infection. From the inhibition patterns the dTk type can be easily established. (See also Table 2 below).

TABLE 2

Detection and typing of viral dTk activity in clinical specimens.

| Sample type | Sample code | Enzyme activity[a] (cpm × 10$^{-3}$) | % Residual enzyme activity after incubation with sera | | | Immunological type of dTk | Clinical diagnosis |
| --- | --- | --- | --- | --- | --- | --- | --- |
| | | | VZV | HSV 1 | HSV 2 | | |
| Vesicle fluid | 1 | 2.5 × 10$^3$ | 17 | 92 | 123 | VZV | Herpes zoster |
| | 2 | 8.1 × 10$^2$ | 7 | 118 | 85 | VZV | Herpes zoster |
| | 3 | 6.6 × 10$^2$ | 6 | 119 | 104 | VZV | Varicellae |
| | 4 | — | — | — | — | — | vesicles non viral orgin |
| | 5 | 7.6 × 10$^1$ | 99 | 89 | 5 | HSV 2 | Genital Herpes |
| | 6 | 5.9 × 10$^2$ | 9 | 127 | 109 | VZV | Varicellae |
| | 7 | 8.8 × 10$^1$ | 101 | 70 | 8 | HSV 2 | Genital Herpes |
| | 8 | 1.2 × 10$^3$ | 11 | 124 | 104 | VZV | Herpes zoster |
| | 9 | 2.3 × 10$^2$ | 107 | 4 | 95 | HSV 1 | Herpes stomatitis |
| | 10 | 1.2 × 10$^1$ | 16 | 89 | 118 | VZV | |
| | 11 | 2.8 × 10$^3$ | 5 | 87 | 91 | VZV | Varicellae |
| | 12 | 6.5 × 10$^2$ | 7 | 109 | 116 | VZV | Varicellae |
| | 13 | 1.5 × 10$^2$ | 10 | 92 | 89 | VZV | Generalized Herpes zoster |
| serum samples | A | 2.8 × 10$^1$ | 18 | | | VZV | Varicellae |
| | B | 1.2 × 10$^2$ | 18 | | | VZV | Varicellae |
| | C | 1.6 × 10$^2$ | 8 | 96 | 85 | VZV | Varicellae |
| | D | 3.4 × 10$^1$ | 12 | 114 | 85 | VZV | Varicellae |
| | E | 4.0 × 10$^1$ | 16 | | | VZV | Varicellae |
| | F | 9.6 × 10$^1$ | 11 | | | VZV | Varicellae |
| control dTk from cultures: | dTkA | 1.0 × 10$^2$ | 120 | 111 | 98 | | |
| | VZV | 8.5 × 10$^1$ | 7 | 106 | 112 | | |
| | HSV 1 | 1.3 × 10$^2$ | 96 | 11 | 94 | | |
| | HSV 2 | 7.5 × 10$^1$ | 112 | 89 | 9 | | |

[a]Activity of control (sample incubated with negative serum) when using 5 μl sample and IUdR at a specific activity of 370 Ci/mmole.

Figure 6:
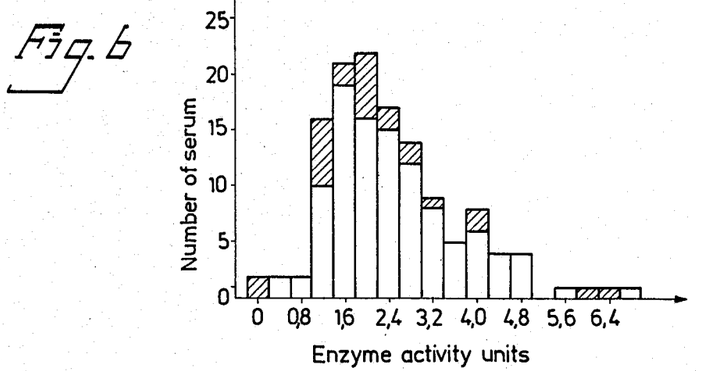
FIG. 6 is a diagram illustrating the normal distribution of dTk activity in blood donors and pregnant women.

One important feature of the invention is thus the drastically increased detection sensitivity, which allows measurement even of normal serum levels of dTk-F in healthy individuals, as can be seen from FIG. 6, which shows the distribution of dTk activity found in sera from 99 blood donors (unfilled columns) and 25 pregnant women in the first trimester (shaded columns). The average is 2.4 units/μl with a standard deviation of 1.25.

Figure 7:
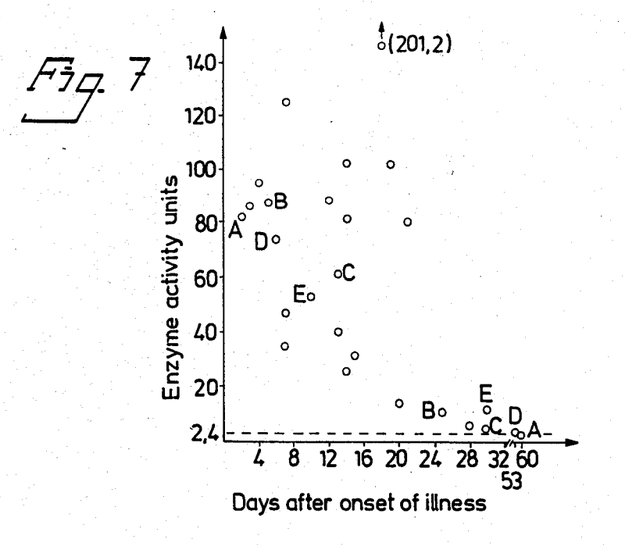
FIG. 7 is a diagram illustrating dTk activities, measured according to the invention, in sera from patients with infectious mononucleosis and related to time after onset of illness.
Figure 8:
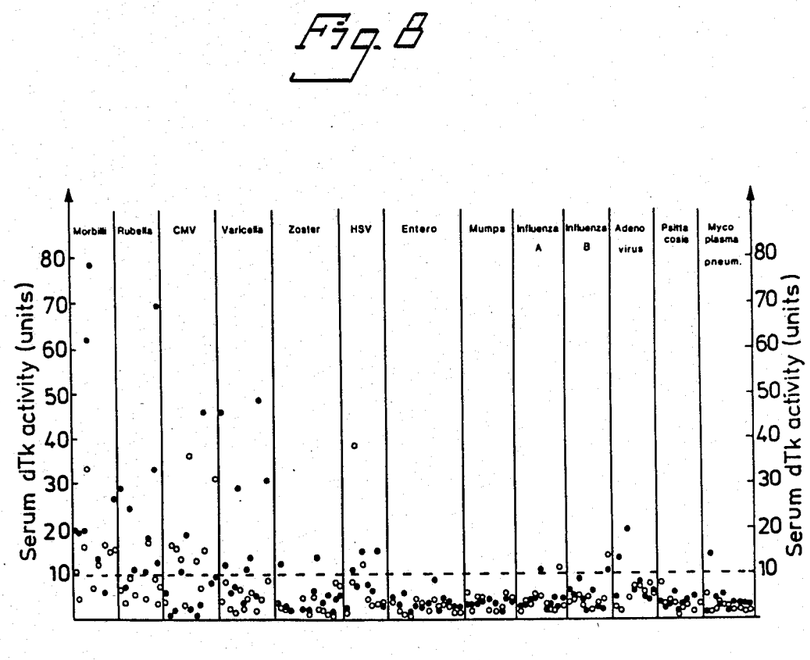
FIG. 8 is a diagram illustrating dTk activities found in sera from patients suffering from various virus infections, mycoplasma pneumoniae, and psittacosis.

Investigations of serum samples from individuals suffering from infectious diseases lead to the discovery of 10–40 times elevated dTk levels in serum from patients in acute stages of certain virus infections, e.g. mononucleosis infectiosa, rubella- and morbillivirus infections. FIG. 7 shows the dTk activity/μl formed in sera from patients with infectious mononucleosis as related to time after onset of illness. Symbols labeled with the same letter indicate sera from the same patient, and the dotted line shows the normal value for healthy individuals. FIG. 8 shows the dTk activity/μl found in acute (●) and convalescent (o) sera of patients suffering from different virus infections, mycoplasma pneumoniae, and psittacosis. The dotted line indicates a value, which is 4 times the normal value for healthy individuals.

Concerning herpes viruses the results indicate elevated serum dTk activities in connection with primary infections. No consequent increases in dTk activities (>10 units) were found in connection with other infections (FIG. 8). The characterization of the serum activities found has hitherto demonstrated the presence of Varicella Zoster Virus (VZV) specific dTk (Table 2) and cell dTk-F. It has also been demonstrated that the claimed method can be used for determining virus specific dTk present in vesicle fluids for rapid diagnosis of infections (Table 2). All serum dTk activities found in connection with viral infections disappeared gradually, reaching normal levels within 2-6 weeks.

Regarding patients suffering from malignant diseases, a limited study, using the assay method according to the invention, showed elevated serum dTk levels not only in patients suffering from malignancies originating from the lympho-proliferative system, but also in patients having malignancies of other cells with metastases in the lymphoproliferative system (see Table 3).

Figure 9A:
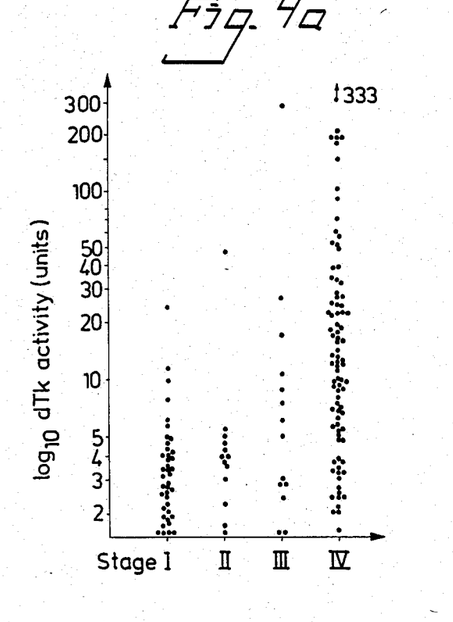
FIGS. 9a and 9b are diagrams illustrating the correlation between serum dTk activity, as measured according to the invention, and the stage of the disease for patients suffering from NHL.
Figure 9B:
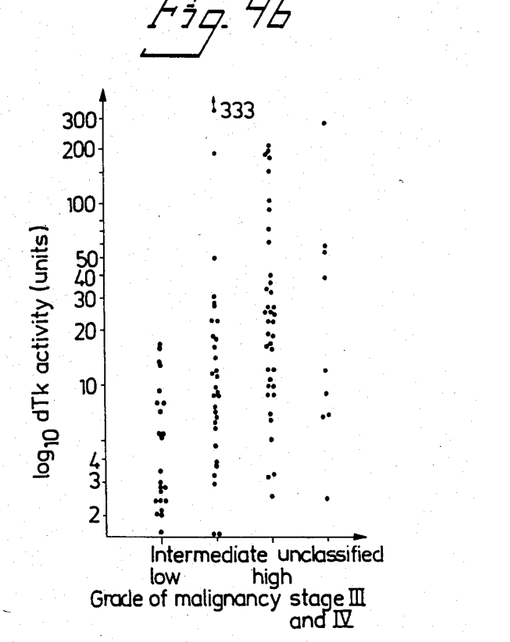

Extended studies have been performed with well defined large serum materials from patients suffering of lympho-proliferative diseases, such as non-Hodgkin's lymphoma (NHL), Hodgin's disease (HD), cronic and activated lymphatic leukemia (CLL) and myelomas. Detailed results in the NHL group were as follows: normal serum dTk and enhanced dTk levels of different magnitude were found. These dTk levels correlated to staging of the disease, (see FIG. 9a which shows serum-dTk in 155 untreated patients with NHL correlated to stage of the disease), i.e., the more advanced disease the higher the dTk values. When the dTk levels were related to the malignancy of the tumour cells (classification according to the Kiel system), then a good correlation between high dTk levels and malignancy was found (see FIG. 9b which shows serum dTk in 101 NHL patients in stages III-IV divided into three stages of malignancy)

TABLE 3 dTk levels in sera from patients with different tumour diseases.

| Type of disease | Status of disease | dTk activity (units/μl) |
|---|---|---|
| Lung cancer[d] | no metastases | 5 |
| Lung cancer | no metastases | 2 |
| Lung cancer | metastases | 163 |
| Lung cancer | metastases | 19 |
| HD | metastases | 108 |
| HD | metastases | 28 |
| HD | no metastases | 4 |
| HD | no metastases | 3 |
| NHL | advanced stage | 333 |
| NHL | advanced stage | 14 |
| NHL | early stage | 3 |
| NHL | early stage | 5 |
| Adenocarcinoma | active | 72 |
| Leukemia | acute | 40 |
| Leukemia | acute | 185 |
| B-cell leukemia | active | 52 |
| CML | active | 3500[a] |
| CML | active | 45 |
| CLL | active | 62 |
| CLL | active | 18 |
| CLL | semiactive | 11 |
| CLL | semiactive | 12 |
| CLL | in active | 2.8[b] |
| Healthy individuals | | 2.4[c] |
| Leukemia acute | no metastase | 0.07[e] |
| Leukemia acute | no metastase | 0.20[e] |
| Leukemia acute | metastase | 1.3[e] |
| Leukemia acute | metastase | 1.6[e] |

Figure 10A:
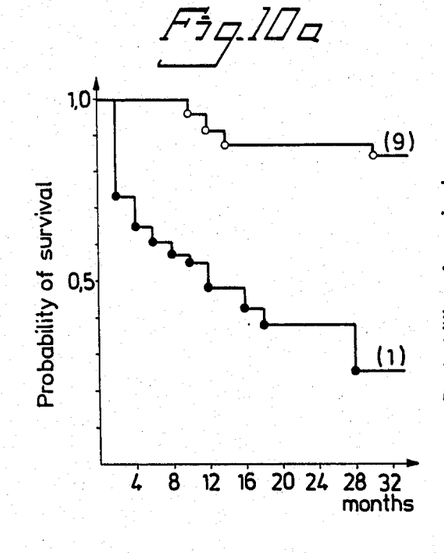
FIGS. 10a and 10b illustrate the probability of survival for NHL patients related to the pretreatment serum dTk levels as measured according to the invention.
Figure 10B:
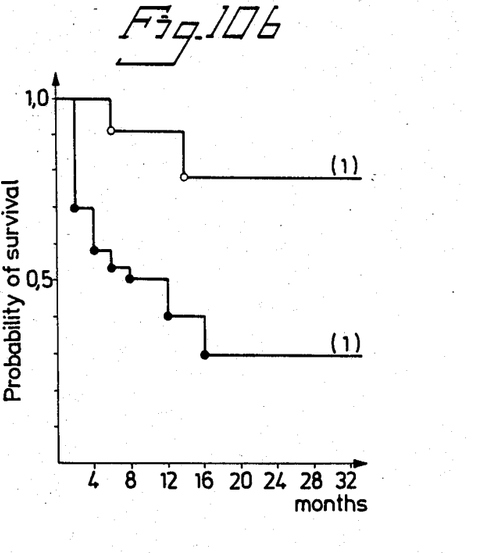

[a]Therapy two days earlier.
[b]Average value from 6 patients; values ranging between 0.5 and 5.4
[c]See previous section.
[d]All lung cancers in this study were of the oat cell type.
[e]determination of dTk activity in spinal fluid, 5 μl undiluted spinal fluid was used per 120 μl final volume in assay.
Abbreviations used;
HD; Hodgkins' disease
NHL; non-Hodgkin's lymphoma
CML; chronic myeloic leukemia
CLL; chronic lymphatic leukemia The utility of the assay method according to the invention for prognostic purposes was demonstrated by highly significant differences in survival times between patient groups constructed by division according to measured dTk values $<10$ units and $>10$ units respectively. FIG. 10a shows the probability of survival for NHL patients in stages III-IV with pretreatment serum dTk $<10$ units (—o—o—, n=50) and $>10$ units (-●-●-, n=51). The numbers in parenthesis indicate remaining individuals at observation after 32 months. FIG. 10b shows the probability of survival for NHL patients in stages III-IV with "high grade" malignancy of tumour. Pretreatment level of serum dTk $<10$ (—o—o, n=11) and $>10$ units (-●—●-, n=27). The numbers in parenthesis indicate remaining individuals at observation after 32 months.

Figure 11:
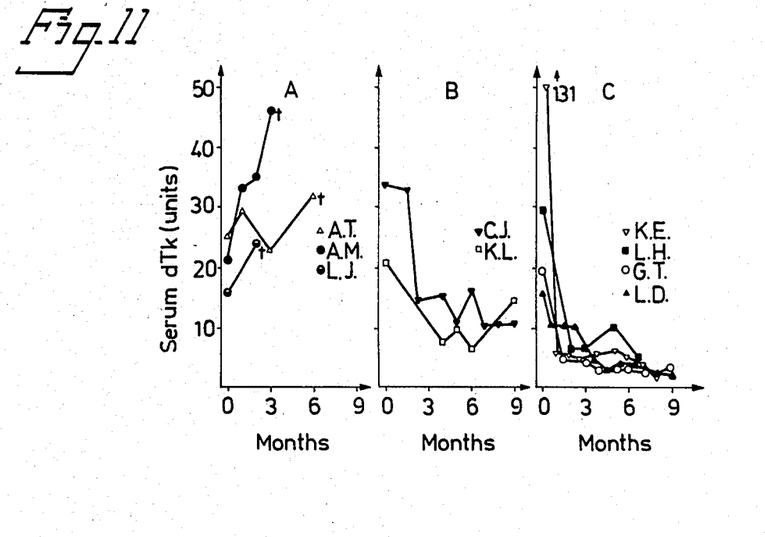
FIGS. 11 and 12 are diagrams illustrating longitudinal studies of serum dTk levels for NHL patients with varying clinical course.
Figure 12:
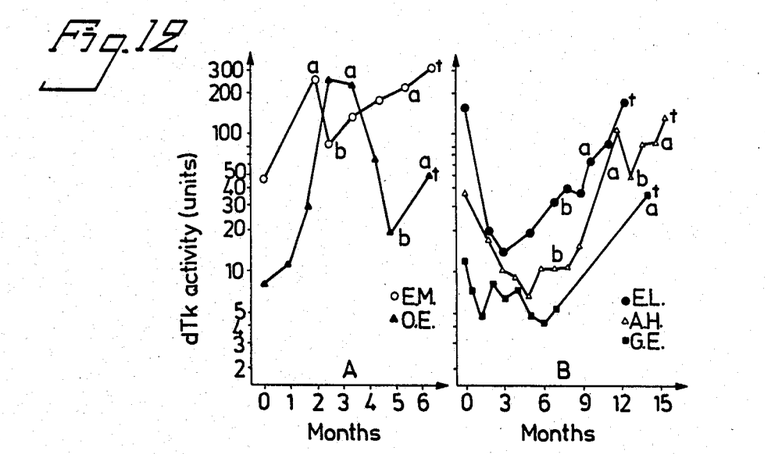

Furthermore, longitudinal studies of serum dTk levels in NHL patients revealed alterations correlating to alterations of the disease, i.e. lower values upon regression of disease, higher upon progression and unaltered in constant disease. FIG. 11 shows the variations in the measured serum dTk levels for A three patients with progressive disease, B two patients treated to partial remission, and C four patients treated to complete remission. In FIG. 12 serum dTk is followed longitudinally in patients, where both progressive disease (a), and remission (b) occur. (A) were two patients with progressive disease, who after change of therapy were treated to partial remission before the disease progressed again. (B) were three patients treated to remission (A. H. and E. L. to partial, and G. E. to complete remission). All of them later relapsed. A. H. responded for a short time once more to therapy. These results clearly show the possibility the effect of therapy, and also to rapidly detect relapses both during and after treatment as increasing dTk values.

When using the assay method according to the invention in connection with the other above mentioned lympho-proliferative diseases variable serum dTk levels were found, e.g. in cronic CLL normal values were found, while half activated CLL gave low but pathological values ($>10$ units), and active CLL high. Possible uses of dTk levels, as examplified for NHL, are also relevant for CLL. Moreover, studies of spinal fluid, derived from patients with leukemia, show presence of dTk when leukemic cells are present in the cerebro-spinal system. Regarding cancer, the results found from patients with lung cancer of the oat cell type indicate the possibility to utilize serum dTk levels as a marker of metastases as well as for other cancers. These conclusions are evident from Table 3.

Naturally one has to be aware of possible transient elevated serum dTk level in patients with malignant disease, due to the above mentioned virus infections. However, these virus diseases are normally contracted in childhood, while malignant tumour diseases commonly is present in adults. Another factor relevant for the use of serum dTk levels for the described purposes, is the rare occurence of elevated dTk activities indicated in a study of an unselected serum material, derived from patients with undefined disease, consecutively obtained for diagnostic purposes. Studies of medical records for these and other patients have shown that neither pathological values in liver function tests, nor leucocytosis are normally accompanied by enhanced serum dTk levels.

We claim:

1. A method of determining dTk isoenzyme levels of a human or animal body fluid or cell sample, comprising the steps of reacting said sample with a substrate for said isoenzyme consisting of 2'-deoxy-5-halouridin, containing a radio-labelled 5-halogen, said substrate being present in a concentration ranging from $2 \times 10^{-9}$ to $5 \times 10^{-6}$M, in the presence of a phosphate donor in a concentration sufficient for producing a measurable amount of phosphorylated product, said concentration not exceeding 20 mM and a buffer system sufficient for maintaining a pH within the range of 5 to 9 in a concentration of no more than 250 mM, and measuring the amount of phosphorylated product formed on said substrate, said amount being proportional to isoenzyme level.

2. A method according to claim 1, wherein said pH is from about 6.5–8, said substrate concentration is from $10^{-8}$–$5 \times 10^{-7}$M, and said phosphate donor concentration is from about 0.5–5 mM.

3. A method according to claim 1 or 2, wherein said buffer substance is essentially free from TRIS-maleate.

4. A method according to claim 1, wherein said phosphate donor is selected from the group consisting of ATP and CTP.

5. A method according to claim 1, further comprising the step of determining available radio-labelled substrate by reacting a control consisting of dTk isoenzyme in an excess sufficient to cause substrate exhaustion, said control being processed in the same manner as said sample before measuring the radioactivity of said phosphorylated product.

6. The method of claim 1, wherein said buffer system comprises N-2-hydroxyethylpiperazine N-2-ethanesulfonic acid.

7. The method of claim 1, wherein said buffer system is devoid of reactive or primary amino groups.

8. The method of claim 1, wherein substrate is $^{125}$I-2-deoxy-5-iodouridine and the concentration of said substrate ranges from $1 \times 10^{-8}$ to $5 \times 10^{-7}$M.

* * * * *